US008979896B2

(12) United States Patent
Barlow et al.

(10) Patent No.: US 8,979,896 B2
(45) Date of Patent: Mar. 17, 2015

(54) PACIFIER SYSTEM FOR STIMULATING AND ENTRAINING THE HUMAN OROFACIAL SYSTEM

(75) Inventors: Steven M. Barlow, Lawrence, KS (US); Donald S. Finan, Boulder, CO (US); Rajesh Vantipalli, Lawrence, KS (US); Raghavendra Shantha, Lawrence, KS (US)

(73) Assignees: University of Kansas, Lawrence, KS (US); Regents of the University of Colorado, Boulder, CO (US)

( * ) Notice: Subject to any disclaimer, the term of this patent is extended or adjusted under 35 U.S.C. 154(b) by 1244 days.

(21) Appl. No.: 11/209,177

(22) Filed: Aug. 22, 2005

(65) Prior Publication Data

US 2006/0079814 A1  Apr. 13, 2006

Related U.S. Application Data

(60) Provisional application No. 60/605,578, filed on Aug. 30, 2004.

(51) Int. Cl.
*A61J 17/00* (2006.01)
*A61B 5/00* (2006.01)
*A61B 5/03* (2006.01)

(52) U.S. Cl.
CPC .......... *A61B 5/682* (2013.01); *A61B 5/038* (2013.01); *A61J 17/00* (2013.01); *A61B 2562/0247* (2013.01)
USPC .......................................................... 606/234

(58) Field of Classification Search
CPC ........................................................ A61J 17/00
USPC ................................................. 606/234–236
See application file for complete search history.

(56) References Cited

U.S. PATENT DOCUMENTS 3,790,016 A   2/1974  Kron
4,232,687 A   11/1980 Anderson-Shanklin
(Continued)

FOREIGN PATENT DOCUMENTS

EP   2082721 A1   7/2009
EP   1786319 B1   10/2012
(Continued)

OTHER PUBLICATIONS

"International Preliminary Report on Patentability (including the International Search Report and Written Opinion) for PCT Application No. PCT/US2005/031169, mailed Dec. 21, 2006", 11 pgs.
(Continued)

*Primary Examiner* — Darwin Erezo
*Assistant Examiner* — Richard Louis
(74) *Attorney, Agent, or Firm* — Schwegman Lundberg & Woessner, P.A.

(57) ABSTRACT

This application discusses systems and method for entraining oromotor pattern development, such as the suck, in the orofacial system of an infant having neurological impairments or developmental disabilities. The system includes a baglet, an entrainment device, and a processor. In varying examples, the system additionally includes one or a combination of: a baglet pressure sensor, a memory, a timing circuit, a valve, a receiver assembly, a display device, and one or more data acquisition, data analysis, and stimulus-control software. Options and variations for each feature of the system are various. The present systems provide patterned, rhythmic stimulation to the infant's orofacial system to stimulate and entrain brain development, such as oromotor pattern development.

26 Claims, 6 Drawing Sheets

(56) References Cited

U.S. PATENT DOCUMENTS

| | | | |
|---|---|---|---|
| 4,505,398 A | | 3/1985 | Kesselring |
| 5,693,073 A | | 12/1997 | Glick et al. |
| 5,830,235 A | * | 11/1998 | Standley ............... 606/234 |
| 6,033,367 A | * | 3/2000 | Goldfield ............... 600/529 |
| 6,120,528 A | | 9/2000 | Link et al. |
| 6,161,710 A | | 12/2000 | Dieringer et al. |
| 6,264,678 B1 | | 7/2001 | Landers |
| 6,468,294 B2 | | 10/2002 | Griffith |
| 6,591,140 B2 | | 7/2003 | Strome et al. |
| 6,966,904 B2 | | 11/2005 | Ruth et al. |
| 6,968,964 B2 | | 11/2005 | Gilmore |
| 7,333,020 B2 | | 2/2008 | Cohen et al. |
| 8,251,926 B2 | | 8/2012 | Barlow et al. |
| 2001/0047189 A1 | | 11/2001 | Griffith |
| 2003/0032984 A1 | | 2/2003 | Hakim |
| 2004/0039358 A1 | * | 2/2004 | Rollin et al. ............... 604/346 |
| 2004/0188372 A1 | * | 9/2004 | Ruth et al. ............... 215/11.4 |
| 2004/0220618 A1 | | 11/2004 | Rohrig |
| 2005/0251211 A1 | | 11/2005 | Knifong |
| 2005/0277987 A1 | | 12/2005 | Randolph et al. |
| 2006/0074354 A1 | | 4/2006 | Barlow et al. |
| 2006/0079814 A1 | | 4/2006 | Barlow et al. |
| 2006/0201901 A1 | | 9/2006 | Sabree et al. |
| 2006/0290517 A1 | | 12/2006 | Cohen et al. |
| 2008/0077183 A1 | | 3/2008 | Cohen |
| 2009/0005810 A1 | | 1/2009 | Bonazza |
| 2010/0137906 A1 | | 6/2010 | Stalling et al. |
| 2010/0308001 A1 | | 12/2010 | Duineveld |

FOREIGN PATENT DOCUMENTS

| | | |
|---|---|---|
| FR | 2729843 | 8/1996 |
| WO | WO-9704736 A1 | 2/1997 |
| WO | WO-0009006 | 2/2000 |
| WO | WO-0100136 A1 | 1/2001 |
| WO | WO-2006/026623 A2 | 3/2006 |
| WO | WO-2006/033801 A1 | 3/2006 |
| WO | WO-2008020349 A1 | 2/2008 |
| WO | WO-2008127733 | 10/2008 |
| WO | WO-2009093173 | 7/2009 |
| WO | WO-2010046812 A1 | 4/2010 |

OTHER PUBLICATIONS

"International Search Report for corresponding PCT Application No. PCT/US2005/030869, mailed Apr. 25, 2006", 7 pgs.

"Written Opinion for corresponding PCT Application No. PCT/US2005/030869 mailed Apr. 14, 2006", 9 pgs.

Andreatta, R. D., et al., "Low-level Static Lip Force Control Does Not Alter Vibrotactile Detection Thresholds in the Human Orofacial System", *Experimental Brain Research*, 151, (2003), 548-552.

Andreatta, R. D., et al., "Movement-Related Modulation of Vibrotactile Detection Thresholds in the Human Orofacial System", *Experimental Brain Research*, 149, (2003), 75-82.

Barlow, S. M., et al., "Actifier II: The Dynamics of Sensorimotor Integration During Suck in Neonates and Infants", *12th Biennial Conference on Speech Motor Control*, Albuquerque, NM,(Mar. 20, 2004), 19 pgs.

Barlow, S. M., et al., "Chapter 9—Sensorimotor Entrainment of Respiratory and Orofacial Systems in Humans", *In: Speech Motor Control in Normal and Disordered Speech*, B. Maassen, et al., Editors, Oxford University Press, (2004), 16 pgs.

Barlow, S. M., et al., "Mechanically Evoked Peroral Reflexes in Infants", *Brain Research*, 599 (1), (1992),158-160.

Barlow, Steven M., et al., "Mechanosensory Modulation of Trigeminofacial Pathways During Speech", *Society for Neuroscience*, 2820, (Nov. 3, 2002), 1 pg.

Barlow, S. M., "Modulation of Mechanically Evoked Perioral Reflexes During Active Force", *Brain Research*, 565(2), (1991),330-336.

Barlow, S. M., et al., "Physiological Studies of the Human Vocal Tract Across the Lifespan", *4th Annual Willard R. Zemlin Award Lecture in Speech Science Session*. 1138., ASHA National Convention, Chicago, IL,(Nov. 14, 2003),56 pgs.

Finan, D. S., et al., "Dynamic Loading of the Developing Human Respiratory System: A New Method", 135-29, ASHA National Convention, Chicago, U.S.A.,(Nov. 13, 2003),3 pgs.

Finan, D. S., et al., "The Actifier: A Device for Neurophysiological Studies of Orofacial Control in Human Infants", *Journal of Speech and Hearing Research*, vol. 39 (1996),833-838.

Seibel, L., et al., "Actifier II: The Dynamics of Non-Nutritive Suck in Neonates and Infants", *12th Biennial Conference on Speech Motor Control*, Albuquerque, NM, Mar. 20, 2004), 8 pgs.

Lau, Chantal, "Oral Feeding in the Preterm", *NeoReviews*, 7 (1), (Jan. 2006), e19-e27.

Pickler, Rita H, et al., "Effects of non-nutritive sucking on nutritive sucking, breathing, and behavior during bottle feedings of preterm infants", *Adv Neonatal Care*, 4(4), (Aug. 4, 2004), 226-34.

"U.S. Appl. No. 11/209,029, Decision on Pre-Appeal Brief mailed Mar. 9, 2011", 2 pgs.

"U.S. Appl. No. 11/209,029, Pre-Appeal Brief filed Dec. 21, 2010", 4 pgs.

"International Application Serial No. PCT/US2005/030869, International Preliminary Report on Patentability mailed Jan. 26, 2007", 13 pgs.

"International Application Serial No. PCT/US2005/031169, Written Opinion mailed Feb. 1, 2006", 6 pgs.

"U.S. Appl. No. 11/209,029 Advisory Action mailed Nov. 12, 2010", 3 pgs.

"U.S. Appl. No. 11/209,029 Final Office Action mailed Jul. 21, 2010", 9 Pgs.

"U.S. Appl. No. 11/209,029, Non-Final Office Action mailed Dec. 24, 2009", 11 pgs.

"U.S. Appl. No. 11/209,029, Response filed Oct. 28, 2010 to Final Office Action mailed Jul. 21, 2010", 11 pgs.

"U.S. Appl. No. 11/209,029, Response filed Apr. 26, 2010 to Non-Final Office Action mailed Dec. 24, 2009", 13 pgs.

"U.S. Appl. No. 11/209,029, Non Final Office Action mailed Aug. 5, 2011", 10 pgs.

"Chinese Application Serial No. 200580036192.0, Office Action mailed Oct. 12, 2010", 6 pgs.

"Chinese Application Serial No. 200580036192.0, Office Action Response Filed Feb. 28, 2011", 12 pgs.

"European Application Serial No. 05814103.7, Office Action mailed Oct. 5, 2010", 4 pgs.

"European Application Serial No. 05814103.7, Office Action Response Filed Apr. 14, 2011", 32 pgs.

Finan, D. S, et al., "The Actifier: A Device for Neurophysiological Studies of Orofacial Control in Human Infants", Journal of Speech and Hearing Research, 39, (Aug. 1996), 833-838.

"U.S. Appl. No. 11/209,029 , Response filed Apr. 23, 2012 to Final Office Action mailed Mar. 1, 2012", 18 pgs.

"U.S. Appl. No. 11/209,029 , Response filed Dec. 5, 2011 to Non Final Office Action mailed Aug. 5, 2011", 11 pgs.

"U.S. Appl. No. 11/209,029, Final Office Action mailed Mar. 1, 2012", 10 pgs.

"U.S. Appl. No. 11/209,029, Notice of Allowance mailed May 11, 2012", 7 pgs.

"U.S. Appl. No. 12/325,850 , Response filed Feb. 13, 2012 to Final Office Action mailed Dec. 13, 2011", 11 pgs.

"U.S. Appl. No. 12/325,850 , Response filed Aug. 29, 2012 to Non Final Office Action mailed Mar. 29, 2012", 11 pgs.

"U.S. Appl. No. 12/325,850, Advisory Action mailed Mar. 9, 2012", 3 pgs.

"U.S. Appl. No. 12/325,850, Final Office Action mailed Dec. 13, 2011", 10 pgs.

"U.S. Appl. No. 12/325,850, Non Final Office Action mailed Mar. 29, 2012", 10 pgs.

"U.S. Appl. No. 12/325,850, Non Final Office Action mailed Dec. 30, 2010", 8 pgs.

"U.S. Appl. No. 12/325,850, Response filed Jun. 29, 2011 to Non Final Office Action mailed Dec. 30, 2010", 15 pgs.

"Chinese Application Serial No. 200580036192.0, Office Action mailed Jan. 31, 2012", With English Translation, 8 pgs.

"Chinese Application Serial No. 200580036192.0, Office Action mailed Jul. 17, 2012", With English Translation, 8 pgs.

(56) References Cited

OTHER PUBLICATIONS

"Chinese Application Serial No. 200580036192.0, Response filed Jun. 15, 2012 to Office Action mailed Jan. 31, 2012", 11 pgs.
"Chinese Application Serial No. 200580036193.5, Office Action mailed Mar. 10, 2009", 6 pgs.
"Chinese Application Serial No. 200580036193.5, Office Action mailed Mar. 16, 2012", With English Translation, 6 pgs.
"Chinese Application Serial No. 200580036193.5, Office Action mailed Apr. 26, 2011", 11 pgs.
"Chinese Application Serial No. 200580036193.5, Office Action Response filed Sep. 13, 2011", 9 pgs.
"Chinese Application Serial No. 200580036193.5, Response filed MAy 31, 2012 to Office Action mailed Mar. 16, 2012", 4 pgs.
"European Application Serial No. 05797922.1, Examination Notification mailed Mar. 25, 2011", 7 pgs.
"European Application Serial No. 05797922.1, Office Action Response filed Aug. 31, 2011", 13 pgs.
"European Application Serial No. 05814103.7, Office Action mailed Jun. 12, 2012", 3 pgs.
"European Application Serial No. 05814103.7, Response filed Aug. 20, 2012 to Office Action mailed Jun. 12, 2012", 26 pgs.
"European Application Serial No. 09252710.0, Extended European Search Report mailed Aug. 31, 2010", 7 pgs.
"European Application Serial No. 09252710.0, Office Action mailed Dec. 5, 2011", 5 pgs.
"European Application Serial No. 09252710.0, Response filed Nov. 11, 2011 to Office Action mailed Jul. 13, 2011", 13 pgs.
"European Application Serial No. 09252710.0, Response filed Mar. 29, 2011", 3 pgs.
"European Application Serial No. 09252710.0, Office Action mailed Jul. 13, 2011", 5 pgs.
Boven, W. Robert, et al., "The limit of tactile spatial resolution in humans: grating orientation discrimination at the lip, tongue, and finger", Neurology, 44(12), (1994), 2361-66.
"U.S. Appl. No. 12/325,850, Non Final Office Action mailed Sep. 11, 2013", 15 pgs.
"Chinese Application Serial No. 200580036192.0, Office Action mailed Apr. 3, 2013", (w/ English Translation), 10 pgs.
"Chinese Application Serial No. 2005800361923, Response filed Jun. 27, 2013 to Office Action mailed Apr. 3, 2013", (w/ English Translation of Claims), 10 pgs.
"Chinese Application Serial No. 200580036192.0, Response filed Dec. 3, 2012 to Office Action mailed Jul. 17, 2012", (w/ English Translation of Amendment Claims), 11 pgs.
"U.S. Appl. No. 12/325,850, Final Office Action mailed Mar. 21, 2014", 15 pgs.
"U.S. Appl. No. 12/325,850, Response filed Mar. 11, 2014 to Non Final Office Action mailed Sep. 11, 2013", 8 pgs.
"Chinese Application Serial No. 200580036192.0, Decision on Rejection mailed Aug. 23, 2013", 8 pgs.

* cited by examiner

PACIFIER SYSTEM FOR STIMULATING AND ENTRAINING THE HUMAN OROFACIAL SYSTEM

CLAIM OF BENEFIT OF PRIOR-FILED APPLICATION

This patent application claims the benefit of U.S. Provisional Application Ser. No. 60/605,578, entitled "Pacifier System for Stimulating and Entraining the Human Orofacial System," filed on Aug. 30, 2004, under 35 U.S.C. §119(e), which is hereby incorporated by reference in its entirety.

STATEMENT AS TO RIGHTS TO INVENTIONS MADE UNDER FEDERALLY SPONSORED RESEARCH AND DEVELOPMENT

The subject matter discussed in this patent application was funded in part by United States Grant No. RO1-DC03311-01 from the National Institute of Health (NIH). The government may have certain rights to the subject matter discussed herein.

CROSS-REFERENCE TO RELATED APPLICATION

This application is related to U.S. patent application, entitled "Pacifier System for Studying and Stimulating the Human Orofacial System," filed even date herewith, which is hereby incorporated by reference in its entirety.

TECHNICAL FIELD

This patent application pertains generally to systems and methods for entrainment of human anatomy, and more particularly to systems and method for entrainment of a human orofacial system.

BACKGROUND

The brain of a typically developing fetus includes an organized set of neurons in the brainstem and cortex that are involved in the production of centrally patterned rhythmic motor behaviors. These neural circuits are known as central pattern generators or simply "CPG's". One such rhythmic behavior that is controlled by a CPG is the suck. Under normal circumstances, the human infant is precocial for suck, which means it is a motor behavior that is established in utero and functional at birth. An infant's ability to suck at birth is important for, among other things, getting nourishment and stimulating the infant's developing brain.

In premature birth, the premature infant loses opportunities for safe neurological development in utero. This loss can be compounded by medical complications associated with premature birth, such as strokes or hemorrhages. Further, medical complications often are treated with painful procedures which correlate with impairment in neurological development. As a result of the impairment in neurological development, the premature infant may possess grossly disorganized CPG's and therefore exhibit grossly disorganized suck, which itself can lead to other medical complications and a failure to thrive and develop. Other ramifications of disorganized suck may include: ramifications relating to the infant's overall sensorimotor development, perceptual capacity, and even delays in higher cognitive function including speech, language, and other processing skills.

This problem affects several hundred thousand babies. Many of these babies suffer with a partially developed nervous system, respiratory system, and/or other anatomy. Many of these neurological impairments and developmental disabilities are not discovered using available diagnostic tools. What are needed are new tools to identify problems earlier. Additionally needed are new tools to overcome disorders.

SUMMARY

The present disclosure includes a system for entraining motor pattern development in an infant's orofacial system. In one embodiment, the system includes a baglet, an entrainment device, and a processor. In varying examples, the system further includes one or a combination of: a baglet pressure sensor, a memory, a timing circuit, a valve, a receiver assembly, a display device, and one or more data acquisition, data analysis, and stimulus-control software.

Options for each feature of the system are various. As an example, in one embodiment the baglet is incorporated into a pacifier and includes a cavity therein. In various embodiments, the entrainment device includes a motor and a pneumatic actuator. In various embodiments, the actuator includes a piston-cylinder assembly. In varying examples, the motor, based on control signals from the processor, causes the actuator to impose rhythmic changes in a size, shape, or intracavity pressure of the baglet, thereby simulating the patterning of neurologically intact suck.

Other options for the system may include, but are not limited to, the following. In some examples, the baglet pressure sensor is a pressure transducer and is capable of sensing, among other things, one or a combination of: a baglet intracavity pressure intensity, a baglet intracavity pressure duration, and a baglet intracavity pressure frequency. In some examples, the receiver assembly provides a pacifier mounting system using a ring-groove configuration. The ring-groove configuration makes attachment and detachment of the pacifier quick and easy for a user (e.g., caregiver). In some examples, the valve is a pneumatic bleed valve used to adjust a generated stimulus in accordance with a predetermined suck regimen received by the processor.

In one embodiment of a method for entraining an infant's suck, the method includes generating an entrainment signal based, at least in part, on a predetermined suck regimen, providing a stimulus to a baglet, and sensing a baglet pressure signal. In many examples, the predetermined suck regimen is based on an assessment of the infant. In varying examples, providing the stimulus includes a patterned, rhythmic stimulus to the infant through excitation of the baglet (e.g., changes in the size, shape, or intracavity pressure of the baglet). In many examples, the method further includes storing a history of the stimulus provided to the infant and monitoring a suck progress of the infant.

In one embodiment of a process for fabricating a system capable of entraining an infant's suck, the process includes coupling a baglet pressure sensor and an entrainment device to a processor and mounting the baglet pressure sensor, the entrainment device and the processor in a system adapted to interface with orofacial tissue. In this process, the entrainment device is configured to receive an entrainment signal synthesized by the processor and transpose the signal into a stimulus applicable to a baglet. In some examples, the process further includes coupling a user input device (e.g., external user interface) to the processor. In one example, coupling the entrainment device to the processor includes coupling a motor to the processor, coupling an actuator to the motor, and pneumatically coupling a baglet back end to the actuator.

Advantageously, with the present systems, it may be possible to help an infant possessing an orofacial deficiency by increasing the infant's functional oromotor behavior and improving the mapping of perception-action subsystems in the infant's developing brain. Further, the present systems may positively impact the infant's subsequent cognitive skills, such as speech. Such advantages may be possible as a result of the present systems' ability to provide patterned, rhythmic stimulation to the infant's orofacial system at pulses which coordinate and time muscle contractions of such infant's orofacial system. Another advantage is that the potential users of the present systems and methods may be various. For instance, neonatalogists, pediatric and Neonatal Intensive Care Unit (NICU) nurses, and developmental speech physiologists may all find utility from the disclosed systems. A further advantage of the present systems is that a "take-home" version may be made for use by parents to help their infant(s) with oromotor difficulties, such as feeding difficulties, resulting from orofacial deficiencies.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

The drawings illustrate generally, by way of example, various embodiments discussed in the present application.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Figure 1:
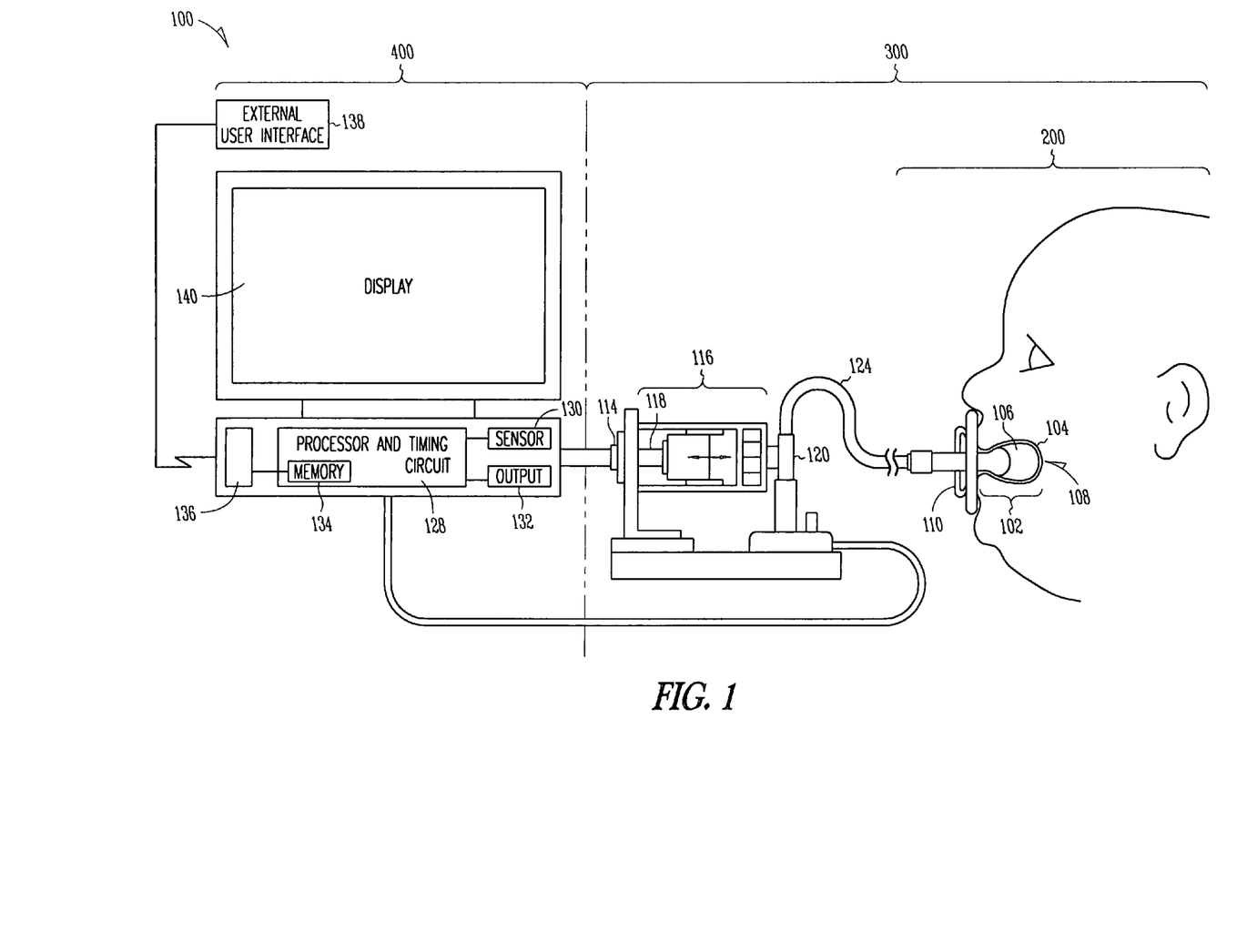
FIG. 1 is a side view illustrating a system as constructed in accordance with at least one embodiment of the present subject matter.

FIG. 1 is a partial side view, having a cut-away, and illustrating an orofacial interaction system 100, according to one embodiment of the present subject matter. In various embodiments, the orofacial interaction system has a first portion 300 and a second portion 400. In various embodiments, the system is adapted for stimulating and entraining motor pattern development, such as the suck, in the orofacial system of an infant having neurological impairments or developmental disabilities. While the present disclosure includes embodiments using a non-nutritive suck, other embodiments additionally fall within the present scope.

In some examples, the first portion 300 of the orofacial interaction system 100 includes a head assembly 200 having a baglet 104. A baglet, in various embodiments, includes a synthetic nipple or nipple-like structure. In various embodiments, the baglet 104 is integrated within a pacifier 102 and includes a cavity 106 therein. The baglet 104, in various embodiments, has a baglet front end 108 and a baglet back end 110. In various embodiments, the baglet front end 108 is adapted to be inserted into an infant's mouth and sucked on by the infant. In one example, the pacifier 102 used in the orofacial interaction system 100 is a medical grade silicon pacifier. One example of such a pacifier is a SOOTHIE pacifier. SOOTHIE is a trademark of Children's Medical Ventures, Inc., which is incorporated in Delaware. Other pacifier makes and models may also be used without departing from the scope of the present subject matter. Various embodiments use pacifiers available in at least three sizes: micro-premature infants, premature infants, and term infants.

Figure 3A:
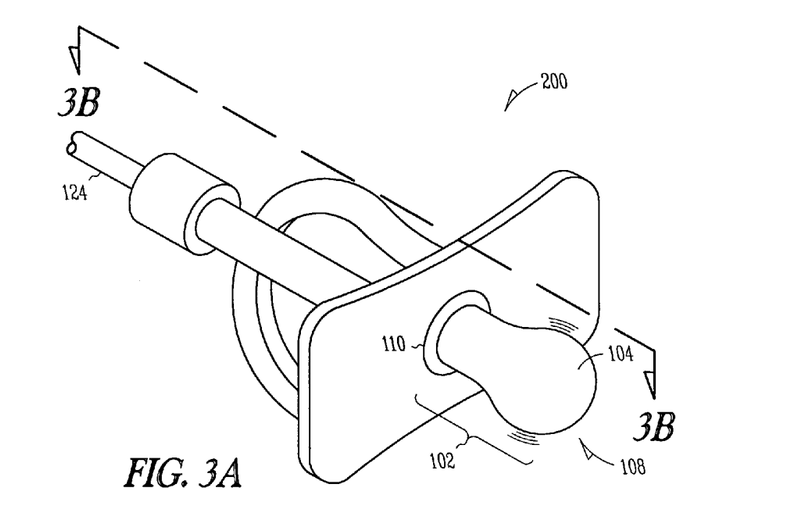
FIG. 3A is a perspective view illustrating an assembly of a portion of a system as constructed in accordance with at least one embodiment of the present subject matter.
Figure 3B:
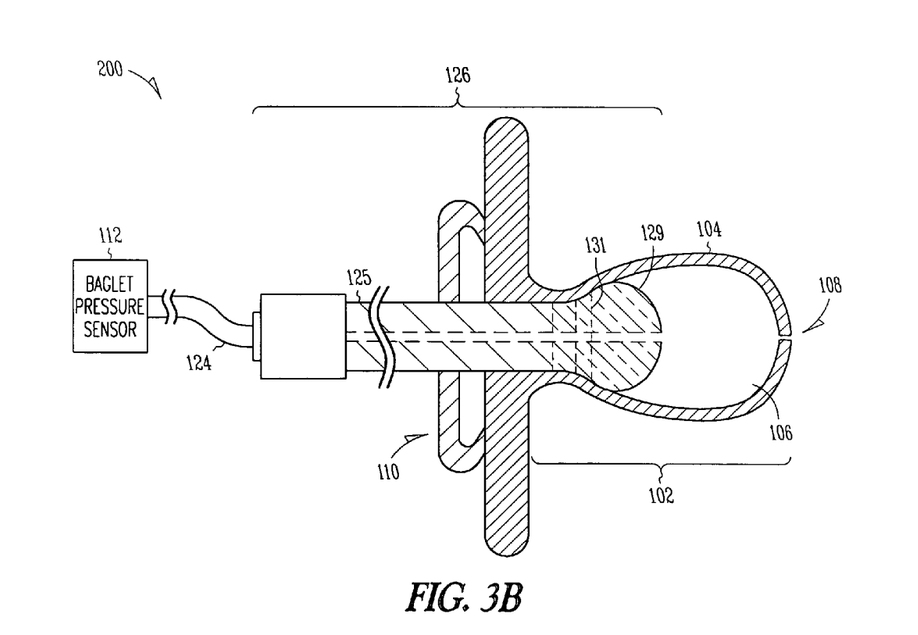
FIG. 3B is a cross-sectional view taken along line 3B-3B of FIG. 3A.

In varying examples of the orofacial interaction system 100, the pacifier 102 is mounted to a receiver assembly. In some embodiments, the receiver assembly is adapted for a demountable attachment of the pacifier 102 by way of a ring-groove configuration. One example of such a configuration is illustrated in FIG. 3. One benefit of the ring-groove configuration is that it allows a user to detach a first pacifier after it is used by a first infant and attach a second pacifier for use by a second infant in a short amount of time. In one example, the receiver assembly is instrumented with a baglet pressure sensor. In such an example, the baglet pressure sensor may be pneumatically coupled with the cavity 106 of the baglet 104 via a pressure line 124.

The baglet pressure sensor may be adapted to sense a baglet pressure signal, which in many examples provides an indication of one or a combination of: a baglet intracavity (e.g., within the baglet's cavity) pressure intensity, a baglet intracavity pressure frequency, and a baglet intracavity pressure duration.

In various embodiments, the first portion 300 of the orofacial interaction system 100 further includes an entrainment device, which is adapted to receive computer instructions and provide a signal to influence a patient mechanically. In some embodiments, the first portion 300 receives an entrainment signal computed by a processor 128 and thereafter delivers a stimulus to the head assembly 200. In some examples, the first portion 300 acts on baglet 104.

In many examples, including FIG. 1, the entrainment device includes a motor 114 and an actuator 116. In one example, the actuator 116 is mechanically coupled to the motor 114 on an actuator first end 118 and pneumatically coupled to the baglet back end 110 on an actuator second end

120. In one example, the actuator 116 includes a piston-cylinder assembly, which is driven by the motor 114. Such a configuration is adapted to convert the entrainment signal computed by the processor 128 into a mechanically created pneumatic stimulation applied to the baglet 10, in various embodiments.

Figure 2:
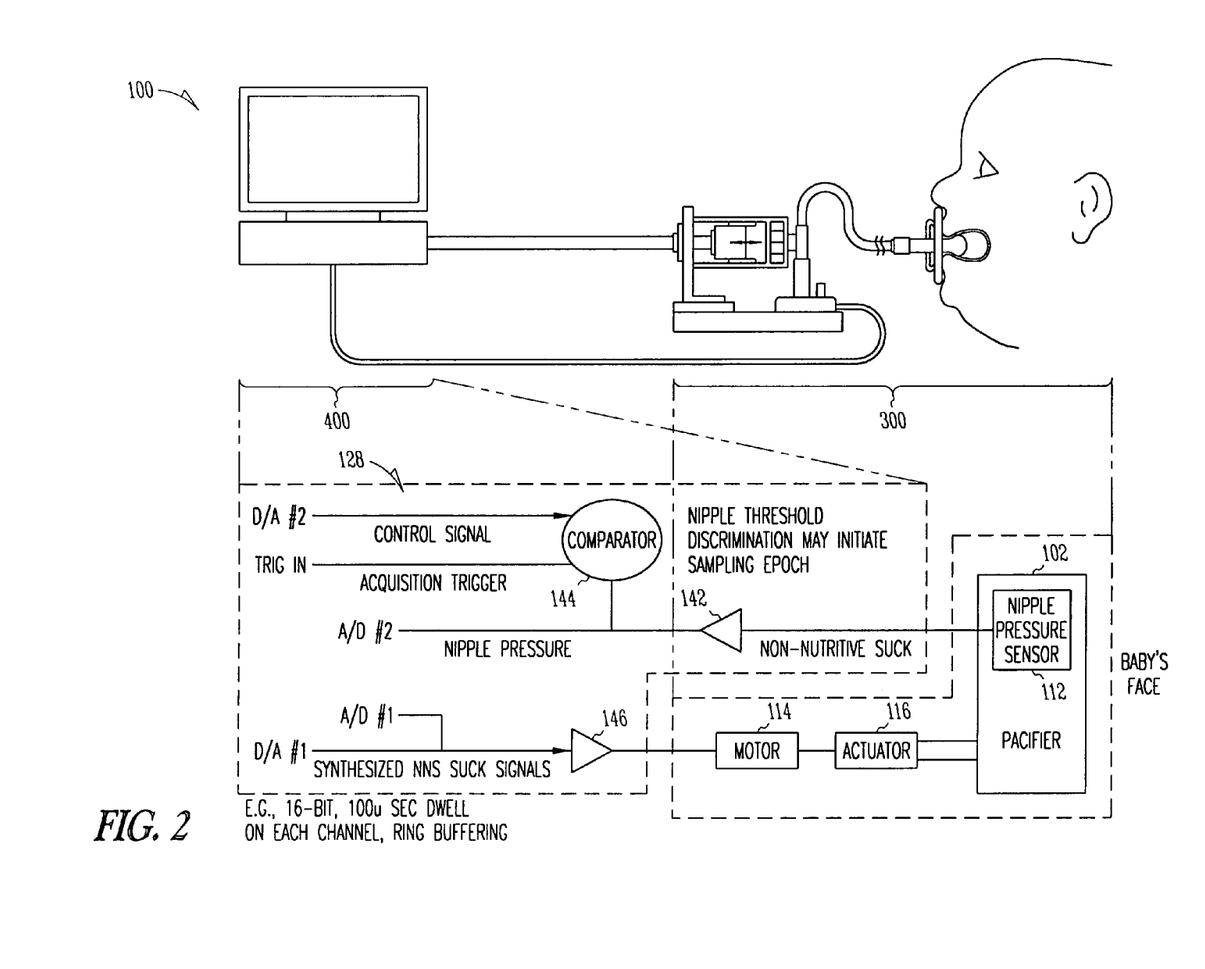
FIG. 2 is a schematic diagram illustrating a system as constructed in accordance with at least one embodiment of the present subject matter.

FIG. 2 illustrates a schematic of a patient interaction device, according to one embodiment of the present subject matter. In various embodiments, a sealed pneumatic coupling between the baglet back end 110 and the actuator second end 120 is achieved via a pressure line 124 (e.g., tubing, such as polyethylene tubing). To achieve proper pressure transduction, the first portion 300 includes a valve in some examples. In one such example, the valve is a quick-release pressure valve and provides for the balancing of the baglet intracavity pressure (re: $P_{atm}$), which is monitored by the baglet pressure sensor 112 (FIG. 3B).

The second portion 400 of the orofacial interaction system 100 includes the processor 128, which as mentioned above, is adapted to compute the entrainment signal communicated to and received by the entrainment device. In many examples, the processor 128 may co-exist with a timing circuit. Additionally, in various embodiments, the processor 128 exists independent of the timing circuit. The timing circuit can be used by the processor 128 to deliver one or more entrainment signals in coordination with the infant's suck or breathing cycles (e.g., the infant's muscle contractions). In various embodiments, the processor 128 is electrically coupled to a baglet pressure sensor to receive the baglet pressure signal. In the example of FIG. 1, the baglet pressure signal is received by a sense detection circuit 130 before being communicated to the processor 128. Thus the processor 128, in various examples, is coupled to the entrainment device to deliver the computed entrainment signal.

In some examples, the entrainment signal is based, at least in part, on the baglet pressure signal. In other examples, the entrainment signal is based, at least in part, on a predetermined suck regimen of the infant. In yet other examples, the entrainment signal is based, at least in part, on both the baglet pressure signal and the predetermined suck regimen.

In various examples, a predetermined suck regimen is found by performing a suck assessment of the infant. For example, a suck assessment can include comparing the infant's suck profile to that of one or more similarly-aged infants who are neurologically intact. This comparison might be between a patient and one or more infants known to not suffer from neurological impairments or developmental disabilities. A suck assessment can diagnose deficiencies in the infant's suck.

In various embodiments, based on the suck assessment, a predetermined suck regimen is computed. Various suck regimens include threshold assessment baglet pressure signals to be therapeutically applied to the baglet 104.

In some examples, the predetermined suck regimen is stored in a memory 134 of the processor 128. In various embodiments, the predetermined suck regimen is communicated to the memory 134 in various ways. In one example, the predetermined suck regimen may be received by a communication circuit 136 coupled to the memory 134. The communication circuit 136, in some examples, is capable of wirelessly communicating with a communication circuit of an external user interface 138. In another example, the predetermined suck regimen may be communicated to the memory 134 by way of an electrically coupled external user interface 138. In various additional examples, the external user interface 138 provides an input device for the user to enter the predetermined suck regimen manually. In yet another example, the memory 134 used in orofacial interaction system 100 may be the same memory used in the determination of the predetermined suck regimen and therefore does not need to be manually entered.

A number of variations exist for orofacial interaction system 100 depending on the factors used in the computation of the entrainment signal. As an example, when the entrainment signal is computed without the use of the predetermined suck regimen, the memory 134 of orofacial interaction system 100 need not be programmed with the predetermined suck regimen. When the entrainment signal is computed without the use of the baglet pressure signal, orofacial interaction system 100 need not include the baglet pressure sensor 112.

In one example, after generating the entrainment signal, the processor 128 communicates the entrainment signal to an output circuit 132. After receiving the entrainment signal, the output circuit 132 communicates the entrainment signal to the entrainment device, which transduces the electrically-based entrainment signal into mechanical activity to influence baglet 104. For example various embodiments change the size of the baglet. Some embodiments change the shape. Some embodiments change the intracavity pressure of the baglet 104. Additional embodiments combine multiple mechanical effects.

Baglet 104 excitation can occur at multiple frequencies. Additionally, signals can influence baglet 104 at multiple amplitudes. In various embodiments, influences to baglet 104 are delivered in accordance with the predetermined suck regimen. In some examples, the processor 128, by way of the output circuit 132, communicates a valve signal to a valve. Additionally, in various embodiments, the processor 128 executes instructions to compute the valve signal such that the stimulus (e.g., changes in the size, shape, or intracavity pressure of the baglet 104) generated by the entrainment device coordinates with the infant's predetermined suck regimen. In another example, the valve is in direct communication with the baglet pressure sensor 112 and thereby directly adjusts a pressure associated with the stimulus, such that the stimulus is in accordance with the predetermined suck regimen thresholds.

In various embodiments, a display means 140 allows data to be viewable by the user. Some embodiments provide viewable data in real time. In various embodiments, the display means 140 demonstrates data sensed by a baglet pressure sensor (e.g., the baglet pressure signal). In various embodiments, the display means 140 demonstrates data computed by the processor 128 (e.g., the entrainment signal). In various embodiments, the display means 140 demonstrates data produced by the entrainment device (e.g., the stimulus). In various embodiments, the display means 140 demonstrates data communicated to the processor 128 (e.g., the predetermined suck regimen). In various embodiments, the display means 140 demonstrates the suck assessment. In one example, the display means 140 is a monitor electrically coupled to the processor 128. In additional examples, the memory 126 is configured to store not only the predetermined suck regimen, but also a history of other information. Examples of data sets that may be stored include: the baglet pressure signal, the entrainment signal, the stimulus experienced by the infant, and the suck assessment. A single data set may be stored in some embodiments. Additional embodiments store multiple data sets. Stored data may provide the user with statistics. For example, in one embodiment, the user can view the infant's progress during the course of treatment.

FIG. 2 is a schematic diagram illustrating a measurement system for a patient, according to one embodiment of the present subject matter. Various embodiments of the present subject matter include an orofacial interaction system 100 having a first portion 300 and a second portion 400. In various embodiments, the system is capable of stimulating and entraining motor pattern development, such as the suck, in the orofacial system of an infant having neurological impairments or developmental disabilities. In one example, the first portion 300 of the orofacial interaction system 100 includes a pacifier 102 having a baglet, a baglet pressure sensor 112, an entrainment device, such as motor 114 and actuator 116, and a processor 128. In many examples, the orofacial interaction system 100 is powered by plugging an attached cord into an electrical outlet, such as into a rolling crib-side laboratory. In other examples, the orofacial interaction system 100 is powered by one or more batteries which may allow for greater mobility. Other powering means may also be employed without departing from the scope of the present subject matter.

In various embodiments, the baglet pressure sensor 112 senses a baglet pressure signal from a cavity of the baglet and provides the baglet pressure signal to the electrically coupled processor 128. In varying examples, the baglet pressure sensor 112 is pneumatically coupled to the pacifier 102. The baglet pressure sensor 112, in various embodiments, is capable of sensing a baglet pressure signal indicative of one or a combination of: a baglet intracavity pressure intensity, a baglet intracavity pressure frequency, and a baglet intracavity pressure duration.

In various embodiments, the baglet pressure signal is amplified by a baglet pressure amplifier 142 to provide an amplified baglet pressure signal. The amplified baglet pressure signal, in various embodiments, is used by a baglet pressure comparator 144 and converted from an analog signal to a digital signal by way of a signal conditioner. The baglet pressure comparator 144 compares the amplified baglet pressure signal sensed to a predetermined suck regimen, in various embodiments.

In one example, after the baglet pressure signal is compared to the predetermined suck regimen (e.g., the threshold baglet pressure signals), the processor 128 executes instructions to compute an entrainment signal, which in turn powers the entrainment device to deliver corrective stimulation to the baglet. In one example, the entrainment signal, before being communicated to the entrainment device, is first sent to a motor amplifier 146 to amplify the entrainment signal. The amplified entrainment signal is, in various embodiments, electrically communicated to the motor 114. The motor 114, in various embodiments, converts the amplified entrainment signal into a mechanical motion which drives the actuator 116. In one example, the driving of the actuator 116 results in pneumatic pressure pulses being delivered to the baglet. In one example, the motor 114 is a linear motor and includes a piston-cylinder assembly. The actuator 116 is mechanically coupled to the motor 114, in various embodiments. As such, the system provides a stimulus in accordance with the predetermined suck regimen.

In one example, the processor 128 stores a real time history of one or a combination of: the assessment of the infant, the predetermined suck regimen, the entrainment signal, the stimulus, and the baglet pressure signal. In one example, the processor 128 is programmed to compute the appropriate entrainment signal which results in the appropriate corrective stimulation being applied to the baglet. In one embodiment, the programming is performed with stimulus-control software. In one embodiment, the program design is based on the predetermined suck regimen. In many examples, the processor 128 is programmed to analyze and display, in real time, one or a combination of: the assessment of the infant, the predetermined suck regimen, the entrainment signal, the stimulus, and the baglet pressure signal. The real time storing, analyzing, and displaying of data may be accomplished by one or more software programs communicated to the processor 128.

In one example, a software program is capable of real time logging and display of the stimulus type and number of non-nutritive stimulus cycles experienced by an infant. In one embodiment, the logged information is deposited in a client database having an integrated memory. In various embodiments, the software provides for processor-based waveform synthesis to produce the desired mechanical stimulus at the baglet 104 based on the predetermined suck regimen. One embodiment includes software which maintains a user-selectable waveform library, with control of stimulus "burst" (e.g., compression and expansion of the baglet) complexity and amplitude.

FIG. 3A is a perspective view of a head assembly, according to one embodiment of the present subject matter. The illustration demonstrates a head assembly 200 of a system for stimulating and entraining motor pattern development. The head assembly is adapted for stimulating and entraining suck in an orofacial system of an infant having neurological impairments or developmental disabilities, for example. In various embodiments, the head assembly 200 may include a pacifier 102 having a baglet 104, a baglet front end 108, and a baglet back end 110, and a pressure line 124. The baglet front end 108 is adapted for insertion into an infant's mouth, in various embodiments. In various examples, after the baglet 104 is inserted into the infant's mouth, the infant may be subjected to a mechanical somatosensory experience generated by an orofacial interaction system. In some of these examples, the pressure line 124 pneumatically couples the head assembly 200 to the rest of the orofacial interaction system.

FIG. 3B is a cross-sectional view taken along line 3B-3B of FIG. 3A. In various embodiments, the head assembly 200 of an orofacial interaction system may include a pacifier 102 having a baglet 104, a baglet front end 108, a baglet back end 110, and a baglet cavity 106, a receiver assembly 126, a pressure line 124, and a pressure sensor 112. In one example, the receiver assembly 126 may be adapted for a detachable coupling of the pacifier 102, such as via a ring-groove configuration. In one example, the detachable coupling is made possible via a receiver assembly 126 including a cannula 125 connecting to a ball 129. In some embodiments, the cannula 15 is stainless steel. Some embodiments use a DELRIN ball 129. DELRIN is a synthetic material and is a registered trademark of the E.I. DuPont de Nemours and Company Corporation, 101 West 10$^{th}$ St., Wilmington, Del. 19898. In various embodiments, the form of the ball 129 is achieved through machining. Other processes for forming a ball additionally fall within the present specification. In various examples, the receiver assembly is ported for intra-baglet cavity 106 pressure transduction. The ball 129, in various embodiments, has a circumferential lip 131 which functions as a retainer for the pacifier 102 at or near a baglet base.

In some examples, the baglet pressure sensor 112 senses a baglet pressure signal from the baglet 104, such as from the cavity 106 of the baglet 104, and provides the baglet pressure signal to a processor. An example processor 128 is depicted in FIG. 2. In varying examples, the baglet pressure signal provides an indication of one or a combination of: a baglet intracavity pressure intensity, a baglet intracavity pressure frequency, and a baglet intracavity pressure duration. In some examples the baglet pressure sensor 112 is in communication with the receiver assembly 126 such that when a pacifier 102 is snapped onto the receiver assembly 126, the baglet pressure sensor 112 is pneumatically connected with the cavity 106. In some embodiments, the snapping function is provided by a ring-groove configuration. In varying examples, the baglet pressure sensor 112 is a pressure transducer. In some examples, the pressure transducer communicates with a valve for proper pressure transduction according to the predetermined suck regimen. The pressure line 124 pneumatically couples to a device on a first end and is pneumatically coupled to the baglet back end 110 on a second end. In one embodiment, the device is an actuator, such as actuator 116 in FIG. 1.

Figure 4A:
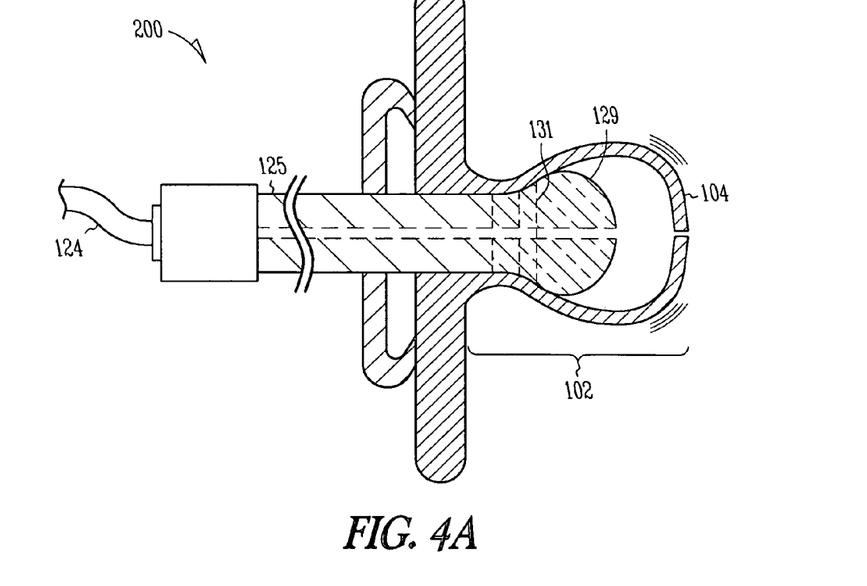
FIG. 4A is a cross-sectional view taken along line 3B-3B of FIG. 3A.
Figure 4B:
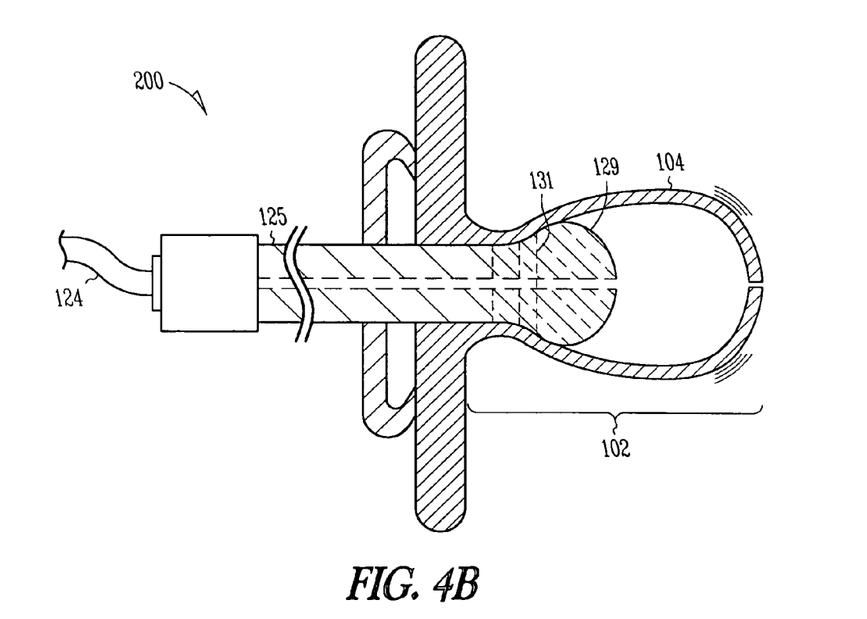
FIG. 4B is a cross-sectional view taken along line 3B-3B of FIG. 3A.
Figure 4C:
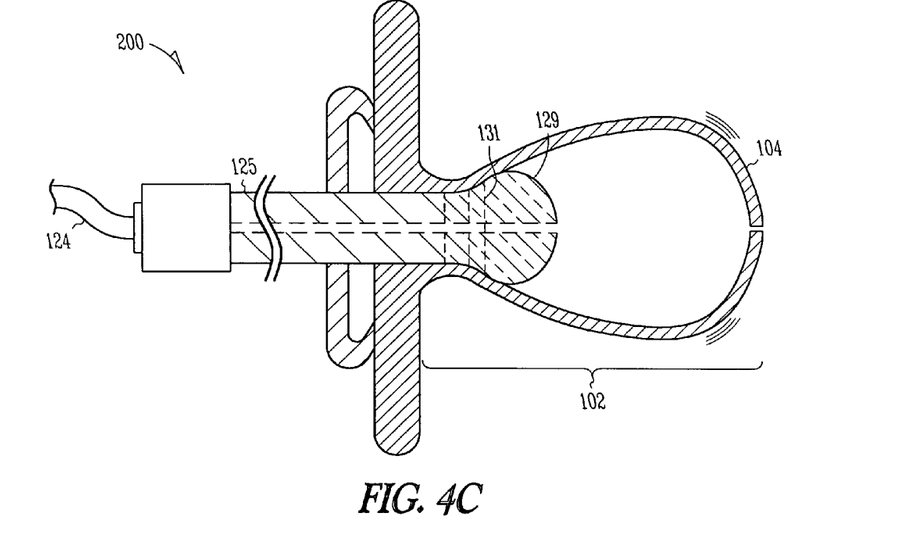
FIG. 4C is a cross-sectional view taken along line 3B-3B of FIG. 3A.

FIGS. 4A, 4B, and 4C represent a baglet in various states, according to various embodiment of the present subject matter. Head assembly 200, in various embodiments, includes baglet 104, which is in sealed, fluid communication with pressure line 124, in various embodiments. Also pictured are: cannula 125; circumferential lip 131; ball 129, and pacifier 102. In various embodiments, pulsating pneumatic pressure in pressure line 124 causes the baglet to expand and contract as illustrated in FIGS. 4A-4C.

The changing of the size, shape, or intracavity pressure of the baglet 104 at synthesized rates provides the infant, specifically the infant's orofacial system, with a patterned, pleasurable, and neurotherapeutic stimulus. In varying examples, the stimulus is mechanically based and produces synchronous excitation of mechanosensory nerve fibers in the infant's lips, tongue, and orofacial tissue, which in turn influences the suck CPG (a neuronal circuit within the infant's central nervous system). It is believed that regular, patterned stimulation delivered by the present system may facilitate development of brain pathways involved in sucking and other rhythmic neural activities. In essence, it is believed that the patterned stimulation may cause the infant's motor output to match the pattern stimulation (applied to the baglet 104) resulting in more highly organized and functional sucking.

Figure 5:
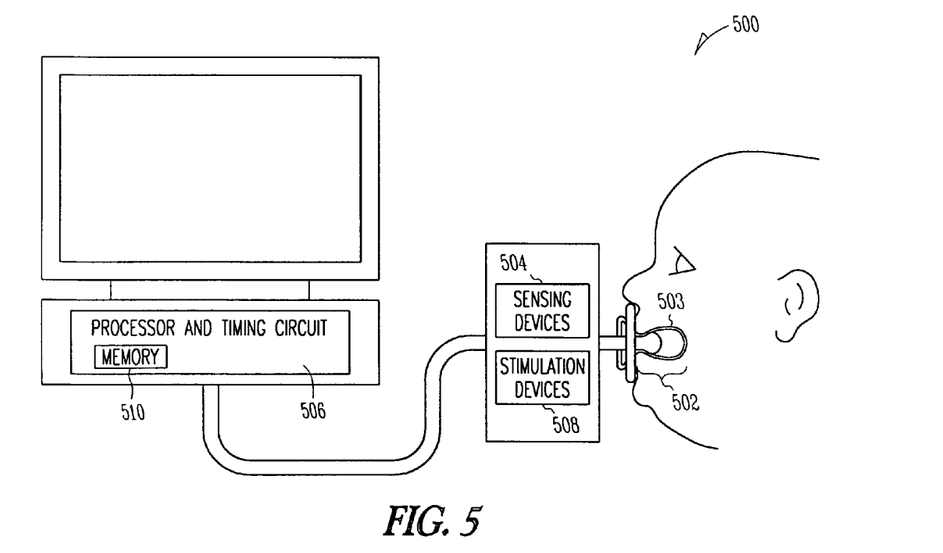
FIG. 5 is a side view illustrating an assessment system for use with a system and a method as constructed in accordance with at least one embodiment of the present subject matter.

FIG. 5 is a side view of an assessment system, according to one embodiment of the present subject matter. In various embodiments, assessment system 500 performs a suck assessment of an infant at risk for or previously diagnosed with neurological impairments or developmental disabilities. In varying examples, the assessment system 500 is capable of determining a suck assessment, which allows for a predetermined suck regimen to be computed. After computation, the predetermined suck regimen may be used with an orofacial interaction system. Various example assessment systems are disclosed in commonly assigned United States patent application entitled, "Pacifier System for Studying and Stimulating the Human Orofacial System", filed even date herewith), which is hereby incorporated by reference in its entirety.

In varying examples, the assessment system 500 includes a pacifier 502 having a baglet 503, one or more sensing devices 504, and a processor 506. In many examples, the assessment system 500 additionally includes one or more stimulation devices 508 and a memory 510. The baglet 503 is adapted to be inserted into the infant's mouth, in various embodiments. One or more sensing devices 504 are configured to sense and provide the processor 506 with data regarding the infant, specifically the infant's orofacial system. The processor 506 is configured to receive and analyze data and also to store data in the memory 510. Based in part on the data provided by one or more sensing devices 504, the one or more stimulation devices 508 are structured to deliver a stimulus to the patient.

In various embodiments, and orofacial interaction system acts as a rehabilitation device therapeutically applied after deficiency(s) are discovered by the assessment system 500. In some examples, an assessment system is in closed-loop communication with an orofacial evaluation system.

It is believed that by first assessing the biomechanics and electrophysiology associated with an infant's suck, any deficiency(s) of the infant's suck can be discovered. Thereafter, the infant may be subjected to a stimulation to correct any deficiency(s) discovered. Following the therapeutic application of one or more stimulations, the infant's suck can again be assessed and evaluated. The cycle can be repeated one or more times, in various embodiments. Such representation demonstrates measurable system efficacy. Such efficacy is useful for patient evaluation. Additionally, such efficacy is used for system configuration evaluation.

Figure 6:
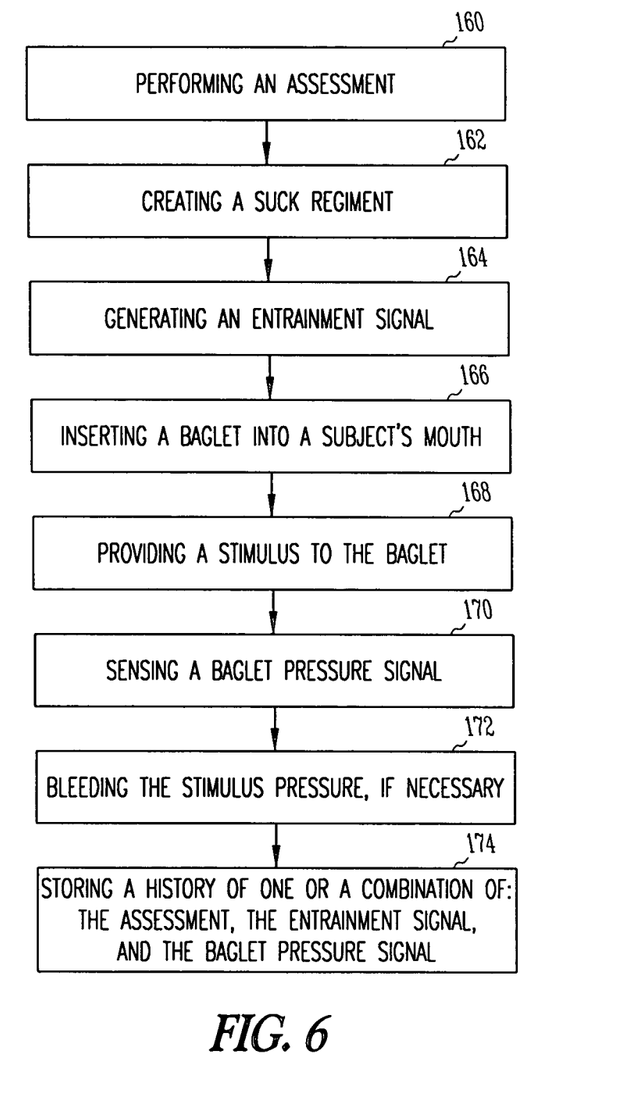
FIG. 6 is a flow chart illustrating a method as constructed in accordance with at least one embodiment of the present subject matter.

FIG. 6 illustrates one example of a method of using an orofacial interaction system, according to one embodiment of the present subject matter. In various embodiment, the present subject matter stimulates and entrains motor pattern development, such as the suck, in the orofacial system of an infant having neurological impairments or developmental disabilities. The method includes performing a suck assessment 160 of an infant, creating a suck regimen 162, generating an entrainment signal 164 based, at least in part, on the suck regimen, inserting a baglet of a pacifier into the infant's mouth 166, providing a stimulus to the baglet 168 based on the entrainment signal, and sensing a baglet pressure signal 170. In some examples, the suck assessment is performed by an assessment system. In some examples, providing the stimulus includes providing a patterned mechanical stimulus to the infant by varying a size, a shape, or an intracavity pressure of the baglet. In some examples, sensing the baglet pressure signal includes sensing one or a combination of: a baglet intracavity pressure intensity, a baglet intracavity pressure frequency, and a baglet intracavity pressure duration.

Several options for the method are possible. For example, the method further includes bleeding a pressure 172 of the stimulus such that the stimulus is balanced (RE: $P_{atm}$) in accordance with predetermined suck regimen thresholds. In varying examples, the method further includes storing a history of one or a combination of: the suck assessment, the predetermined suck regimen, the entrainment signal, the stimulus, and the baglet pressure signal 174. In varying examples, the method further includes analyzing or displaying one or a combination of: the suck assessment, the predetermined suck regimen, the entrainment signal, the stimulus, and the baglet pressure signal. In one example, the method further includes performing a suck assessment at a time after subjecting the infant to the stimulus. In one such example, the method may further include adjusting the entrainment signal, and accordingly the stimulus, based on this later suck assessment. In varying examples, the method further includes monitoring the infant's suck progress using one or both of: the suck assessment(s) and the predetermined suck regimen.

A method of assembling a system to stimulate and entrain motor pattern development, such as the suck, in the orofacial system of an infant having neurological impairments or developmental disabilities is provided. The method includes coupling a baglet pressure sensor configured to sense a baglet pressure signal and an entrainment device structured to receive an entrainment signal to a processor. The method further includes mounting the baglet pressure sensor, the entrainment device, and the processor in a system adapted to interface with orofacial tissue (e.g., infant's lips, mouth, or other facial parts). In varying examples, the entrainment device is structured to convert the entrainment signal into a mechanically created pneumatic stimulus applied to a baglet. In many examples, coupling the entrainment device to the processor includes electrically coupling a motor to the processor, mechanically coupling an actuator to the motor on an actuator first end, and pneumatically coupling a baglet back end to the actuator on an actuator second end.

Several options and variations for the method are possible without departing from the present teachings. For example, various embodiments include an actuator having a piston-cylinder assembly. Thus, mechanically coupling the actuator to the motor includes mechanically coupling a piston-cylinder assembly first end to the motor. Likewise, pneumatically coupling the baglet back end to the actuator includes, in various embodiments, pneumatically coupling the baglet back end to a piston-cylinder assembly second end. In some examples, the method further includes communicatively coupling an external user input device to the processor to receive a predetermined suck regimen of an infant.

Although certain brands and models of components are set forth herein, it is noted that many brands, models and types of components are contemplated and such various embodiments do not depart from the scope of the present disclosure. Further, it is preferable to sterilize all components of the system that come into contact with the infant. One way to sterilize, among many, is by the use of ethylene oxide.

Advantageously, the present systems and methods may help an infant possessing one or more orofacial deficiencies by increasing functional oromotor behavior, improving the mapping of perception-action subsystems in the infant's developing brain, and positively impacting later occurring cognitive development, such as speech. As discussed above, the premature infant is often deprived of the opportunity to continue neurological development in the safe, nurturing environment of a mother's womb and may thus be thrust into an environment using a partially developed nervous system, immature lungs and respiratory system, and emerging anatomy. The present systems and methods provide an external mechanosensory stimulus which may be used to "trigger" and regulate the rate and phase of an infant's suck pattern to entrain such suck to be comparable to one or more similarly-aged infants who are neurologically intact.

The present systems and methods may provide various other benefits as well. For instance, the system may return information to a user regarding the amount of stimulus cycles the infant has experienced and keep a log of the infant's suck progression. The suck progression may provide an indication on how well the infant is responding to the stimulation provided by the system (e.g., efficacy of the system). Further, infants using the present systems and methods may have higher IQs than their counterparts who were not introduced to the systems and methods.

Study

The present systems and methods are currently being implemented at two neonatal intensive case units (NICUs). The NICUs participating in the study include: Stormont-Vail Regional Health Center in Topeka, Kans. and Kansas University Medical Center in Kansas City, Kans. The study is designed to subject infants suffering from neurological impairments or developmental disabilities of the orofacial system to the present systems and methods 3-4 times per day for 5-10 minutes at a time until the infant reaches oromotor competence. It is believed that through the use of the present systems and methods, each subjected infant will develop a suck profile comparable to similarly-aged infants who are neurologically intact.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments will be apparent to those of skill in the art upon reviewing the above description. The scope of the present subject matter should be determined with reference to the appended claims, along with the full scope of equivalents to which such claims are entitled.

What is claimed is:

1. A non-nutritive system for use with a subject, the system comprising:
    a pacifier comprising a baglet, adapted for non-nutritive sucking on by the subject;
    a baglet pressure sensor, adapted to sense a baglet pressure signal;
    a memory, adapted to store a predetermined suck regimen;
    a processor, adapted to receive the baglet pressure signal and the predetermined suck regimen, and adapted to provide an entrainment signal;
    an entrainment device, adapted to receive the entrainment signal, and adapted to provide a stimulus to the baglet; and
    a valve in communication with the baglet, the valve adapted to controllably adjust one or more of: size or shape of the baglet using signals including a signal received from the processor or the baglet pressure sensor,
    wherein the entrainment signal is based, at least in part, on the baglet pressure signal and the predetermined suck regimen.

2. The system as recited in claim 1, wherein the baglet pressure signal provides an indication of one or a combination of: a baglet intracavity pressure intensity, a baglet intracavity pressure frequency, and a baglet intracavity pressure duration.

3. The system as recited in claim 1, wherein the predetermined suck regimen is based, at least in part, on an assessment of the subject.

4. The system as recited in claim 1, wherein the entrainment device comprises:
    a motor, adapted to receive the entrainment signal; and
    an actuator, mechanically coupled to the motor to generate the stimulus.

5. The system as recited in claim 4, wherein the actuator includes a piston-cylinder assembly operable by the motor.

6. The system as recited in claim 4, wherein the baglet is pneumatically coupled to the actuator to receive the stimulus.

7. The system as recited in claim 1, further comprising a timing circuit, adapted to coordinate a timing of the entrainment signal with one or both of: a subject's suck cycle and a subject's breathing cycle.

8. The system as recited in claim 1, wherein the valve is adapted to adjust the stimulus in accordance with the predetermined suck regimen.

9. The system as recited in claim 1, further comprising a receiver assembly, adapted for detachably coupling the baglet.

10. The system as recited in claim 1, wherein the baglet pressure sensor is a pressure transducer.

11. The system as recited in claim 1, wherein the memory is adapted to store a history of one or a combination of: an assessment of the subject, the predetermined suck regimen, the entrainment signal, the stimulus, and the baglet pressure signal.

12. The system as recited in claim 1, further comprising a display device adapted to illustrate one or a combination of:

an assessment of the subject, the predetermined suck regimen, the entrainment signal, the stimulus, and the baglet pressure signal.

13. A non-nutritive system for mechanically entraining an orofacial system of a subject, the system comprising:
 a pacifier comprising a baglet, adapted for non-nutritive sucking on by the subject;
 a baglet pressure sensor, adapted to sense a baglet pressure signal;
 a processor, adapted to receive the baglet pressure signal, and adapted to provide an entrainment signal;
 an entrainment device, adapted to receive the entrainment signal, and adapted to provide a stimulus to the baglet; and
 a valve in communication with the baglet, the valve adapted to controllably adjust one or more of: size or shape of the baglet using signals including a signal received from the processor or the baglet pressure sensor,
 wherein the entrainment signal is based, at least in part, on the baglet pressure signal.

14. The system as recited in claim 13, wherein the entrainment device comprises:
 a motor, adapted to receive the entrainment signal; and
 an actuator, coupled to the motor to generate the stimulus.

15. The system as recited in claim 14, wherein the baglet is pneumatically coupled to the actuator to receive the stimulus.

16. The system as recited in claim 13, further comprising at least one memory storage device adapted to store a history of one or a combination of: the entrainment signal, the stimulus, and the baglet pressure signal.

17. The system as recited in claim 13, further comprising means for displaying, in real time, one or a combination of: the entrainment signal, the stimulus, and the baglet pressure signal.

18. The system of claim 13, wherein the entrainment signal is based, at least in part, on a predetermined suck regimen.

19. The system as recited in claim 18, wherein the entrainment device comprises:
 a motor, coupled to the processor; and
 an actuator, coupled to the motor.

20. The system as recited in claim 19, wherein the baglet is coupled to the actuator to receive the stimulus.

21. A method of operating a non-nutritive system for generating non-nutritive stimulus for a subject comprising:
 generating an entrainment signal based, at least in part, on a predetermined suck regimen;
 providing a mechanical stimulus to a baglet in a pacifier using the entrainment signal, wherein providing the mechanical stimulus includes providing a patterned mechanical stimulus to the baglet by varying one or a combination of: a size of the baglet or a shape of the baglet;
 sensing a baglet pressure signal;
 computing a correction to the entrainment signal with a processor using electronic comparisons of the baglet pressure signal to the predetermined suck regimen; and
 providing a corrected mechanical stimulus to the baglet using the correction to the entrainment signal.

22. The method as recited in claim 21, further comprising storing a history of one or a combination of: an assessment of the subject, the predetermined suck regimen, the entrainment signal, a stimulus provided to the baglet, and the baglet pressure signal.

23. The method as recited in claim 21, further comprising analyzing one or a combination of: an assessment of the subject, the predetermined suck regimen, the entrainment signal, a stimulus provided to the baglet, and the baglet pressure signal.

24. The method as recited in claim 21, further comprising displaying one or a combination of: an assessment of the subject, the predetermined suck regimen, the entrainment signal, a stimulus provided to the baglet, and the baglet pressure signal.

25. The method as recited in claim 21, further comprising monitoring a suck progress of the subject using one or both of: an assessment of the subject and the predetermined suck regimen.

26. The method as recited in claim 21, wherein sensing the baglet pressure signal includes sensing one or a combination of: a baglet intracavity pressure intensity, a baglet intracavity pressure frequency, and a baglet intracavity pressure duration.

* * * * *